Figure 1:
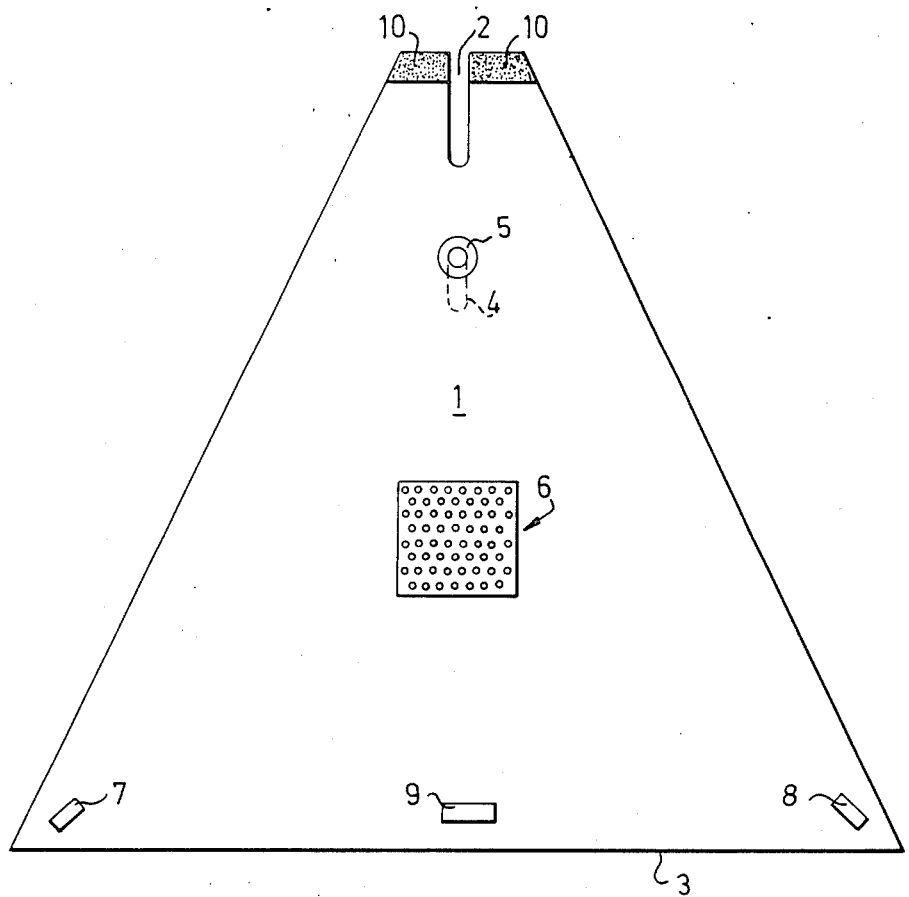

United States Patent [19]

Starzmann

[11] Patent Number: 4,690,137
[45] Date of Patent: Sep. 1, 1987

[54] SUBSTANTIALLY TRIANGULAR SURGICAL DRAPE

[75] Inventor: Martin Starzmann, Gothenburg, Sweden

[73] Assignee: Molnlycke AB, Gothenburg, Sweden

[21] Appl. No.: 797,832

[22] Filed: Nov. 13, 1985

[30] Foreign Application Priority Data

Nov. 21, 1984 [SE] Sweden .............................. 84058650

[51] Int. Cl.⁴ ............................................. A61B 19/08
[52] U.S. Cl. ................................................ 128/132 D
[58] Field of Search ................... 128/132 D; 604/356, 604/357

[56] References Cited

U.S. PATENT DOCUMENTS

| | | | |
|---|---|---|---|
| 3,693,618 | 9/1972 | Madden | 128/132 D |
| 3,923,052 | 12/1975 | Zoephel | 128/132 D |
| 4,043,328 | 8/1977 | Cawood, Jr. et al. | 128/132 D |
| 4,378,794 | 4/1983 | Collins | 128/132 D |
| 4,414,968 | 11/1983 | Amin | 128/132 D |
| 4,471,769 | 9/1984 | Lockhart | 128/132 D |

Primary Examiner—Richard T. Stouffer
Attorney, Agent, or Firm—Young & Thompson

[57] ABSTRACT

The invention relates to a surgical drape suited for use in urethra surgical procedures. The drape is used in combination with a surgical sheet used for covering the torso and legs of the patient, with the patient's legs placed in a raised divergent attitude while the surgeon operates a substantially triangular shape and in that fastenings are provided at the corners of the triangle, these fastenings preferably having the form of a double-sided adhesive tape or coatings of bonding agent or pressure-sensitive adhesive substances. Those fastenings provided at the base corners of the triangle are intended to be secured to the surgical sheet in the vicinity of the lower legs or feet of the patient, and the fastening at the other corner at the site of the operation, so that the surgical drape hangs from its three corners in the shape of a bowl.

3 Claims, 3 Drawing Figures

SUBSTANTIALLY TRIANGULAR SURGICAL DRAPE

The present invention relates to a surgical drape which is intended for surgical procedures performed on the urethra and which is used in combination with a surgical sheet, which may comprise a single piece of material or several separate pieces and which is used to cover the torso and legs of a patient, with the patient's legs being raised and bent in a widely divergent attitude while the surgeon performs a surgical procedure therebetween.

When performing surgery on the urethra, it is, of course, particularly essential that the site of the operation is sterilely isolated from the surroundings, and in particular from the patient's rectum. To this end there is used a surgical drape which is secured with adhesive tape to the backside and to the crutch area of the patient. The surgical drape has located therein an aperture through which the penis of a male patient is drawn and a rubber palpating stall for sterile palpation of the rectum. Although when used in combination with a surgical sheet, a drape of this kind enables the site at which an operation is to be performed to be covered sterilely in a highly efficient manner, it does not afford satisfactory coverage on the part of the theatre personnel present during the operation. For example, when performing prostatic operations, which are highly common in elderly males, large quantities of liquid are liable to squirt from the patient and splash onto the theatre personnel. When performing prostatic surgery, the prostate tissue is namely peeled away and the thus removed tissue constantly flushed or washed away with liquid. This liquid together with released urine makes such surgical procedures troublesome and most unpleasant. The only auxiliary device known hitherto for collecting the liquid thus released is a vessel which is held manually or placed on the operating table in an intended location. The liquid emitted during a prostate operation is namely passed through a filter device, in order to retrieve prostate tissue, which is later analysed.

At present there is no known device for protecting theatre personnel from urine splashes or washing liquid when performing surgical procedures on the urethra.

The present invention, however, provides a surgical drape which eliminates the aforesaid problems.

A surgical drape according to the invention and suited for the aforesaid purpose is mainly characterized in that it is substantially triangular in shape; in that an aperture for the penis of a male patient is provided in one corner of the drape; in that a palpation stall is located at a suitable distance, in the order of 10–15 cm, from said one corner in a direction towards the side, the base, located opposite thereto; in that the base has a length of substantially 1.5 m and the two remaining sides of the triangle have substantially the same length as the base; in that fastening means are provided at the corners of the triangle, said fastening means preferably having the form of double-sided adhesive tape or pressuresensitive adhesive coatings, of which fastening means those provided at the base corners are intended to be fastened to the surgical sheet in the proximity of the lower part of the patient's legs, or the feet of the patient, subsequent to bringing said aperture and said palpation stall to their intended positions, so that the drape hangs from its three corners in the shape of a bowl. As a result of the particular design of the surgical drape according to the invention, the drape is able to collect urine splashes and washing liquid in the relatively wide and large bowl-shaped receptacle formed by the drape when in use, thereby effectively protecting personnel in the close vicinity of the drape from liquid splashes.

A surgical drape according to the invention particularly suited for prostate surgery may have a liquid-permeable central region serving as a filter for straining off tissue removed or released during surgery, this liquid-permeable-region comprising, for example, perforations or a net located in the centre of the drape.

Other embodiments of a surgical drape according to the invention are set forth in the following claims.

Figure 2:
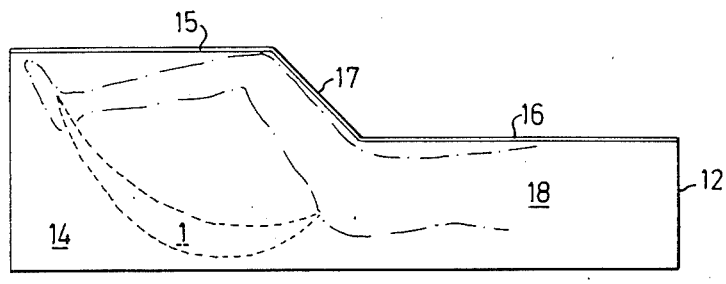
Figure 3:
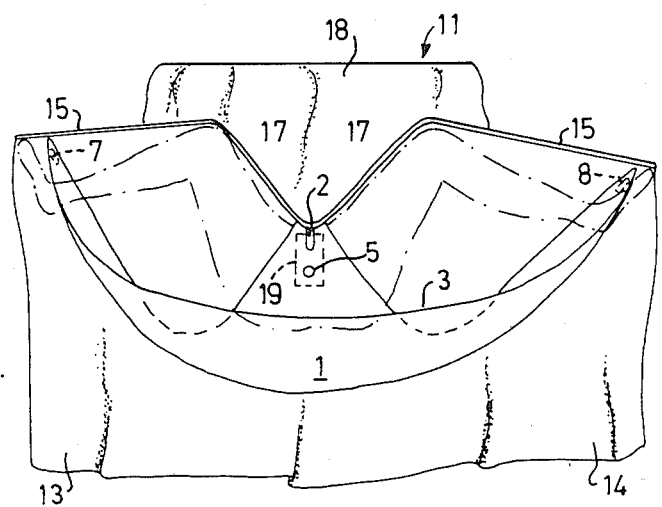

The invention will now be described in more detail with reference to an embodiment thereof illustrated in the accompanying drawings. In the drawings, FIG. 1 is a plan view of a suitable embodiment of a surgical drape according to the invention;

FIG. 2 is a side view of the surgical drape when used in combination with a known surgical sheet of the kind described in the introductory paragraph of the present description; and FIG. 3 is a view of the surgical drape of FIG. 2 when seen in a direction towards the site of the surgical operation.

As clearly shown in FIG. 1, a surgical drape according to the invention may have the general shape of an equilateral triangle, having a side length of suitably 1.5 m. The drape is suitably made from a material comprising a plastics layer laminated with a layer of non-woven material (fibre fabric).

Located in one corner of the drape is a slot 2 which is placed around the penis of a patient. Arranged at a distance of 10 cm from the slot 2, in a direction towards the opposite side, or the base 3, of the drape, is a rubber palpation stall 4, which is firmly connected to the drape 1 by means of an annulus 5. The illustrated surgical drape 1 has provided in the center thereof a perforated area 6, which is intended to serve as a filter means for straining-off tissue removed in prostate surgical procedures. Fastening means 7,8 are provided at the two corners of the base 3. These fastening means suitably have the form of a double-sided adhesive tape, with which the drape can be hung when in use. A further piece of double-sided adhesive tape 9 is provided centrally of the base 3 of the drape. This enables the base 3 to be shortened, by gathering and folding the central part of the base 3 and securing the tuck with the aid of the tape 9.

The drape is provided on both sides of the slot 2, on the non-woven fabric side of the drape, with a bonding agent or pressure sensitive adhesive 10, which is covered with release paper, this paper being removed when the drape is to be secured to the patient.

FIG. 2 illustrates the surgical drape of FIG. 1 when used in combination with a known surgical sheet 11. The illustrated sheet comprises a single one-piece length of sheet blank which has been folded double around its transverse center line, whereafter the continuous end part formed by thus folding the sheet has been folded-in towards the opposite end 12, which is open as a result of the fold, therewith to form two legs 13,14. Subsequent to being thus folded, the sheet blank has been clipped or cut lengthwise, from the open end 12 up to the legs 13,14 formed when folding the blank, while keeping parallel with the longitudinal axis of the blank, and then obliquely outwards towards one edge 15 of the blank and respective legs. The straight and obliquely cut edges are referenced 16 and 17 respectively. The folded and cut or clipped sheet blank has then been joined along the long edges 15 and the oblique edges 17 of respective legs. In this way there is formed firstly a rectangular sheet portion 18 which, as shown in FIGS. 2 and 3, covers the patient above the legs and hangs over the anaesthetics arch, normally located in the close proximity of the operating table, and secondly the legs, 13,14 which are substantially tent-like and cover the legs of the patient and the area around which the surgical procedure is performed. The illustrated sheet has been provided with a working aperture 19 in the crotch region between the legs 13,14, this aperture being formed either prior to folding the sheet blank or subsequent thereto. The legs of the patient are shown in chain lines in FIGS. 2 and 3, and FIG. 3 is a perspective view seen towards the site at which the surgical procedure is to be performed.

As clearly shown in FIGS. 2 and 3, a surgical drape 1 according to the invention is hung between the two leg coverings 13,14 of the surgical sheet 11 covering the diverging legs of the patient. The actual vertical drape 1 is positioned around the patient, with the patient's penis drawn through the slot 2, and is secured to the patient with the aid of the pressure-sensitive adhesive portions or bonding portions 10 located on both sides of the slot 2. The palpation stall 4 is then inserted into the patient's rectum, whereafter the two base corners of the surgical drape are secured by means of the adhesive tapes 7,8 on the surgical sheet 11, centrally between the feet of the patient. As a result thereof the surgical drape 1 according to the present invention will hang from its three corners in the form of a basin, as clearly shown in FIGS. 2 and 3.

The invention is not restricted to the described and illustrated embodiment. For example, pieces of adhesive tape may also be provided along the two remaining side edges of the drape, therewith enabling said sides to be shortened so as to deepen the bowl-like configuration created by the drape.

I claim:

1. A surgical drape which is intended for surgical procedures on the urethra and which is adapted to be used in combination with a surgical sheet, which surgical sheet comprises a piece of material used to cover the torso and legs of a patient with the patient's legs raised and bent in a widely divergent attitude while the surgeon operates therebetween, characterized in that the surgical drape (1) has a substantially triangular shape; that an aperture (2) for the patient's penis is located in one corner of the drape; that a palpation stall (4) is located at a suitable distance from said one corner in a direction towards the side of the drape opposite said one corner; that said opposite side has a length in the order of 1.5 m and the remaining two sides of the triangle are of substantially the same length as the base; that fastening means (7,8,10) are provided in the corners of the triangle, of which fastening means those (7,8) provided at the corners at the ends of said opposite side are adapted, subsequent to bringing the aperture (2) and the palpation stall (4) into their respective positions, to be secured to a said surgical sheet (11) in the vicinity of the lower extremities of the patient, so that the surgical drape (1) hangs from its three corners in the shape of a bowl.

2. A surgical drape according to claim 1, characterized in that the drape is provided in the center thereof with a liquid-permeable area (6), the said area serving as a filter means for straining-off tissue freed during the operation.

3. A surgical drape according to claim 1, said aperture being in the form of an elongated slot whose length is perpendicular to said opposite side, said slot being closed at its end nearest said opposite side and open at its end farthest from said opposite side, and means for selectively securing said drape to a patient with said securing means being positioned adjacent said open end of said slot.

* * * * *